United States Patent [19]

Katsaros et al.

[11] Patent Number: 5,630,833
[45] Date of Patent: May 20, 1997

[54] DEVICE FOR SEALING HEMOSTATIC INCISIONS

[75] Inventors: Georges Katsaros, Jupille, Belgium; David G. Thomas, Town and Country; Richard D. Allison, St. Louis, both of Mo.

[73] Assignee: Sherwood Medical Company, St. Louis, Mo.

[21] Appl. No.: 409,787

[22] Filed: Mar. 24, 1995

Related U.S. Application Data

[63] Continuation of Ser. No. 915,472, Jul. 16, 1992, Pat. No. 5,413,571.

[51] Int. Cl.$^6$ .................................................. A61B 17/00
[52] U.S. Cl. ........................... 606/213; 128/887; 604/51; 604/285
[58] Field of Search .................................. 606/213, 215, 606/216; 128/887; 604/51, 59, 60, 285, 286; 600/32; 623/11, 12

[56] References Cited

U.S. PATENT DOCUMENTS

| | | |
|---|---|---|
| 581,235 | 4/1897 | Kenyon . |
| 1,191,736 | 7/1916 | Roberson . |
| 1,794,221 | 2/1931 | Washburn et al. . |
| 2,898,913 | 8/1959 | Ritter et al. . |
| 3,016,895 | 1/1962 | Sein . |
| 3,056,408 | 10/1962 | Brown . |
| 3,447,533 | 6/1969 | Spicer . |
| 3,516,403 | 6/1970 | Cournut . |
| 3,572,335 | 3/1971 | Robinson . |
| 3,587,586 | 6/1971 | Kronenthal . |
| 3,675,639 | 7/1972 | Cimber . |
| 3,804,097 | 4/1974 | Rudie .................................. 604/51 |
| 3,874,388 | 4/1975 | King et al. . |
| 4,007,743 | 2/1977 | Blake . |
| 4,154,226 | 5/1979 | Hennig et al. . |
| 4,182,339 | 1/1980 | Hardy, Jr. . |
| 4,364,392 | 12/1982 | Strother et al. . |
| 4,390,018 | 6/1983 | Zukowski . |
| 4,453,930 | 6/1984 | Child ................................... 604/59 |
| 4,577,631 | 3/1986 | Kreamer . |
| 4,578,061 | 3/1986 | Lemelson ............................ 604/164 |
| 4,587,969 | 5/1986 | Gillis . |
| 4,588,395 | 5/1986 | Lemelson ............................ 604/59 |
| 4,610,248 | 9/1986 | Rosenberg . |
| 4,619,261 | 10/1986 | Guerriero . |
| 4,638,803 | 1/1987 | Rand . |
| 4,645,488 | 2/1987 | Matukas ............................... 604/59 |
| 4,669,474 | 6/1987 | Barrows . |
| 4,708,718 | 11/1987 | Daniels ................................. 604/53 |
| 4,710,192 | 12/1987 | Liotta et al. .......................... 623/1 |
| 4,744,364 | 5/1988 | Kensey . |
| 4,749,689 | 6/1988 | Miyata et al. ........................ 514/21 |
| 4,774,091 | 9/1988 | Yamahira et al. ................... 424/426 |
| 4,790,819 | 12/1988 | Li et al. ............................... 604/59 |
| 4,829,994 | 5/1989 | Kurth . |
| 4,832,688 | 5/1989 | Sagae et al. ......................... 604/53 |

(List continued on next page.)

FOREIGN PATENT DOCUMENTS

| | | |
|---|---|---|
| 0482350 | 4/1992 | European Pat. Off. . |
| 0493810 | 7/1992 | European Pat. Off. . |
| 1509023 | 4/1978 | United Kingdom . |
| 1569660 | 6/1980 | United Kingdom ................. 604/57 |
| 9014796 | 12/1990 | WIPO . |
| 9109641 | 7/1991 | WIPO ................................. 604/49 |
| 9205740 | 4/1992 | WIPO . |

Primary Examiner—Jeffrey A. Schmidt
Attorney, Agent, or Firm—Montgomery W. Smith; Richard D. Allison

[57] ABSTRACT

A device for sealing incisions in the body of a patient wherein the device includes a bioabsorbable sealing member having an elongate shaft member and an elastomeric and flexible balloon member. The device may also include a preformed or injectable collagenous material associated therewith to hemostatically seal the incision in the body of the patient. The shaft member may include one or more lumens extending therethrough in flow communication with one or more balloon members thereon to provide a relatively simple device which effectively seals an incision in the body of a patient.

12 Claims, 7 Drawing Sheets

U.S. PATENT DOCUMENTS

| | | | |
|---|---|---|---|
| 4,838,280 | 6/1989 | Haaga . | |
| 4,850,960 | 7/1989 | Grayzel | 604/158 |
| 4,852,568 | 8/1989 | Kensey . | |
| 4,871,094 | 10/1989 | Gall et al. | 222/386 |
| 4,878,906 | 11/1989 | Lindemann et al. | 623/1 |
| 4,890,612 | 1/1990 | Kensey | 606/213 |
| 4,895,564 | 1/1990 | Farrel | 604/164 |
| 4,900,303 | 2/1990 | Lemelson | 604/54 |
| 4,929,246 | 5/1990 | Sinofsky | 606/8 |
| 4,941,874 | 7/1990 | Sandow et al. | 604/60 |
| 4,950,234 | 8/1990 | Fujioka et al. | 604/60 |
| 4,994,028 | 2/1991 | Leonard et al. | 604/60 |
| 5,021,059 | 6/1991 | Kensey et al. | 606/213 |
| 5,041,090 | 8/1991 | Scheglov et al. | 606/195 |
| 5,053,046 | 10/1991 | Janese | 606/215 |
| 5,061,274 | 10/1991 | Kensey | 606/213 |
| 5,108,407 | 4/1992 | Geremia et al. | 606/1 |
| 5,108,421 | 4/1992 | Fowler | 606/213 |
| 5,129,882 | 7/1992 | Weldon et al. | 604/53 |
| 5,176,692 | 1/1993 | Wilk et al. | 606/151 |
| 5,350,399 | 9/1994 | Erlebacher et al. | 606/213 |
| 5,370,660 | 12/1994 | Weinstein et al. | 606/215 |
| 5,391,183 | 2/1995 | Janzen et al. | 606/213 |
| 5,403,278 | 4/1995 | Ernst et al. | 604/60 |

DEVICE FOR SEALING HEMOSTATIC INCISIONS

This is a continuation of application Ser. No. 07/915,472 now U.S. Pat. No. 5,413,3571 filed on Jul. 16, 1992 and is co-pending with Ser. No. 08/381,805 filed on Feb. 1, 1995.

FIELD OF THE INVENTION

The present invention relates generally to hemostatic devices and more particularly to an insertion assembly and sealing device which are insertable into an incision or puncture formed in the body of a patient to seal the incision or puncture from the flow of fluids therethrough.

BACKGROUND OF THE INVENTION

During catheterization procedures, the nurse or physician will create an opening into an artery or other vessel with a conventional catheter introducer or dilator. The size of the opening will vary depending on the type of procedure and the size of the catheter which is used. For example, the diameter of the catheter and catheter sheath used in standard angiography procedures is typically between 5 to 8 French (1.67 mm and 2.67 mm, respectively). The diameter of the catheter and catheter sheath used in angioplasty procedures may be 8 (2.67 mm) or 9 (3.33 mm) French. The diameter of the catheter and catheter sheath used in intra-aortic balloon pump procedures is typically between 14 to 16 French (4.67 mm and 5.33 mm, respectively) and the diameter of the catheter and catheter sheath used with cardiopulmonary support systems is typically between 18 and 20 French (6.0 mm and 6.67 mm, respectively). Additionally, the catheter is often twisted or otherwise manipulated as it is advanced to the treatment site, thereby causing a further enlargement of the incision or puncture in the body of the patient.

When the medical procedure is completed and the catheter is removed from the artery or other blood vessel, conventional practice has been to apply external pressure to the entry site until clotting occurs. Because many of the patients undergoing these procedures have been medicated with an anticoagulant such as heparin, the nurse may be required to apply external pressure to the incision site for an extended period of time. The time required to stop bleeding at the incision is not an efficient use of the nurses time and a painful hematoma or unsightly bruise may still occur at the incision site because the artery will continue to bleed internally until clotting blocks the opening in the artery.

U.S. Pat. No. 4,829,994 granted to Kurth on May 16, 1989 attempts to resolve the above-described problem by providing an apron-like device consisting of a pelvic apron and a groin strap to apply a compressive force to the femoral vessel of the patient. Although this device effectively eliminates the need to have a nurse apply direct pressure to the incision site, the decrease in blood flow through the femoral artery caused by the use of this device may increase the likelihood of thrombosis formation in the compromised patient.

Another approach to resolving the above-identified problem is disclosed in U.S. Pat. No. 4,929,246 granted to Sinofsky on May 29, 1990. The method of using the device disclosed in this patent includes the steps of advancing a semi-rigid tube having an inflatable balloon at its distal end through the overlying tissue to a location adjacent to the outer lumen of the punctured artery. The balloon is then inflated to apply pressure directly to the outer lumen of the artery. Laser energy is then directed to the outer lumen of the artery via an optical fiber centrally located in the semi-rigid tube such that the laser energy passes through the optical fiber and balloon of the semi-rigid tube to thermally weld the artery and seal the incision. Finally, the semi-rigid tube and balloon are removed from the incision.

A further approach to resolving the above-identified problem is disclosed in U.S. Pat. No. 4,744,364 granted to Kensey on May 17, 1988 and related U.S. Pat. Nos. 4,852,568, 4,890,612 and 5,021,059 granted to Kensey on Aug. 1, 1989, Jan. 2, 1990 and Jun. 4, 1991, respectively. The first two Kensey patents disclose a device for sealing an opening in the wall of a blood vessel which consists of an elongate tubular body having an anchor member removably disposed therein. The tubular body also includes an ejecting device disposed within the tubular body for forcing the anchor member from the tubular body into the interior of the blood vessel. A retraction filament is secured to the anchor member so that the engagement surface of the anchor member hemostatically engages the inner surface of the blood vessel contiguous with the puncture. The third Kensey patent discloses a device which includes a plug member having a holding portion which is adapted to engage portions of the tissue adjacent to the punctured vessel or organ to hold the plug member in place and a sealing portion formed of a foam material which extends into the punctured vessel or organ to engage the tissue contiguous therewith to seal the puncture. The final Kensey patent discloses a device which includes a pair of members which are positioned along the inner and outer surfaces of the blood vessel wall to seal the puncture.

None of the prior art devices teach the use of a simple, safe and relatively inexpensive means for effecting the closure of a puncture or incision in the wall of a blood vessel.

SUMMARY OF THE INVENTION

Accordingly, it is an object of the present invention to provide a device and method of use which overcomes the disadvantages of the prior art.

It is another object of the present invention to reduce the time required for sealing an incision in an artery and to decrease the likelihood that a hematoma will form after the catheter is removed from the incision.

These and other objects of the present invention are achieved by providing a device and a method for sealing an incision in a blood vessel, duct or lumen using the device as described hereinafter.

One form of the present invention preferably includes a relatively small diameter bioabsorbable sealing member having a balloon member thereon. The sealing member preferably includes a shaft portion formed of a bioabsorbable material having a stiffness sufficient to allow the sealing member to be manipulated through the incision and into the blood vessel prior to the inflation of the balloon member. The balloon member may be formed of a bioabsorbable material preferably having greater flexibility than the shaft member such that the balloon member may be easily manipulated into the blood vessel of the patient prior to the inflation thereof. The balloon member may be inflated with a fluid such as saline solution which preferably includes a radiopaque material therein to allow for the visualization of the balloon member during insertion. Once the balloon member is inflated, the sealing member may be withdrawn in the incision until the proximal side of the balloon member contacts the inner wall of the blood vessel generally adjacent to the incision. In this form of the invention, the balloon member seals the incision to prevent the flow of blood from the blood vessel from entering the incision.

The sealing member is preferably formed of a material which will degrade in the body of the patient over a period of weeks and which will ultimately become absorbed into the body of the patient. As the sealing member degrades, the balloon portion of the sealing member will degrade and harmlessly release the saline solution and radiopaque material into the blood stream of the patient. Once the sealing member is properly positioned in the incision, a collagen or other bioabsorbable plug member may be inserted into the proximal end of the lumen of the sealing member to retain the fluid in the sealing member until the sealing member hemostatically seals the incision. Alternately, the fluid may be removed from the balloon member once hemostasis has been achieved in the incision to minimize the risk that the patient may have an allergic reaction to the release of the radiopaque material.

In an alternate form of this invention, a bioabsorbable collagen member may be used in combination with the sealing member described above. In this embodiment, the collagen member may be formed as an elongate and tubular member which is slid down the shaft of the sealing member once the balloon member is inflated and positioned within the blood vessel of the patient. The collagen member is shaped to slide down the shaft of the sealing member until it contacts the outer wall of the blood vessel or reaches a predetermined position in the incision. The collagen member is formed of a material which swells when it comes into contact with fluids from the body of the patient so that the collagen expands against the resilient tissue surrounding the tissue and so that the collagen contacts and engages the shaft of the sealing member to retain the catheter member in the desired position in the incision.

In a further embodiment of the present invention, the sealing member includes a pair of balloon members on the distal end thereof. The balloon members are positioned on the distal end of the shaft such that when the balloon members are inflated, the balloons extend generally laterally from the shaft member. This positioning of the balloon members enables the distal end of the shaft member to be positioned in the blood vessel to provide a greater resistance to the inadvertent removal of the balloon sealing members from the blood vessel and so that the balloon members extend into the blood vessel a smaller distance than with the single balloon member described above.

In yet another embodiment of the present invention, the shaft member of the sealing member has a pair of lumens extending therethrough and includes a pair of balloon members which are spaced apart laterally along the distal portion thereof. The balloon members are preferably separately inflatable to enable the user to position the distal end of the shaft member in the blood vessel and then inflate the distal balloon member. Once the sealing member is withdrawn in the blood vessel such that the proximal side of the distal balloon member is positioned adjacent to the inner wall of the blood vessel, the second balloon member may then be inflated to form a sealing arrangement along the inner and outer walls of the blood vessel. The sealing arrangement formed by the balloon members seals the incision from the flow of blood through the blood vessel. In a variation of this embodiment, the second balloon member is positioned proximally of the distal end of the shaft member to enable a collagen member to be positioned between the second balloon member and proximally of the outer wall of the blood vessel. In this variation, the proximal balloon member is positioned proximally of the outer wall of the blood vessel to form a sandwich having tissue and the wall of the blood vessel between the respective balloon members. This collagen member may be formed of a semi-rigid cylinder of collagen or may be formed of an injectable collagen which is preferably injected into the incision through a third lumen in the shaft member of the sealing member.

An advantage of the present invention is that it does not require the manipulation of a solid anchor member from the insertion assembly into a predetermined position in the blood vessel. Additionally, it is less likely that a balloon member will separate from the shaft portion of the catheter member than it is for an anchor member to separate from a suture.

A further advantage of the present invention is that the balloon members may be filled with a radiopaque or other contrast media which enables the user to visually observe the position of the sealing member as the present invention is inserted into the incision and blood vessel of the patient.

A further advantage of the present inventions is that as the balloon members degrade, the radiopaque material will be harmlessly released into the blood stream of the patient.

Yet another advantage of the present invention is that it is relatively simple to use and the likelihood that it will be misused or will form a hematoma at the incision site is minimized.

Yet another advantage of the present invention is that it seals the wall of the blood vessel to prevent the formation of a hematoma in the incision.

DETAILED DESCRIPTION OF THE PRESENT INVENTION

The present invention is described hereinafter with specific reference to the use of the present invention for sealing an incision or puncture in a blood vessel such as the femoral artery 10 of a patient. It is contemplated that the present invention may be used with nearly any catheterization or other medical procedure such as laparoscopic or other minimally or less invasive surgeries wherein it is desirable to seal an incision or puncture in the patient to prevent the loss of the patient's body fluid therethrough. As used herein, the distal end of an element is referred to as the end of the element nearest to the patient and the proximal end of an element is referred to as the element furthest away from the patient.

In order to more fully understand and appreciate the present invention, a brief description of a conventional angiographic catheterization procedure through the femoral artery 10 of the patient is set forth herein. In such a procedure, an angiographic needle (not shown) is inserted percutaneously through the epidermal and dermal layer of the skin 12 of the patient at a preferred angle of approximately 25 to 45 degrees. The needle is inserted between 6 mm and 70 mm percutaneously into the skin of the patient until the needle pierces the wall of the femoral artery. The puncture of the artery by the needle is then confirmed by the physician and a small diameter guide wire (not shown) is inserted through the needle for approximately 15 to 20 cm. The needle is then withdrawn over the guidewire while pressure is applied to the artery 10 to limit the bleeding and prevent the formation of a hematoma at the incision site. The catheter (not shown) and an outer introducer or catheter sheath 14 are inserted over the guidewire and the guidewire is then removed from the inside of the catheter. Next, the catheter is advanced to the final location and the procedure is performed. Once the procedure has been completed, the catheter is removed and only the catheter sheath 14 remains in the incision to allow the present invention to be inserted into the incision as described hereinafter.

Figure 1:
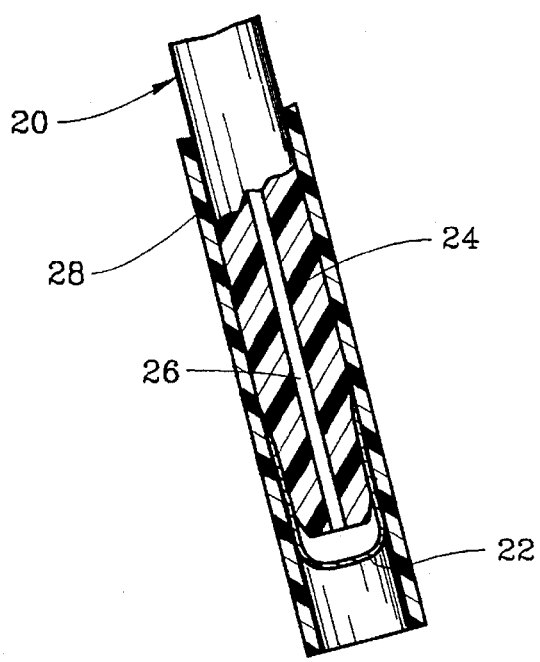
FIG. 1 is a side elevational view, partially in cross section, showing the present invention in an insertion sheath prior to insertion of the sealing member into the incision in the patient.
Figure 3:
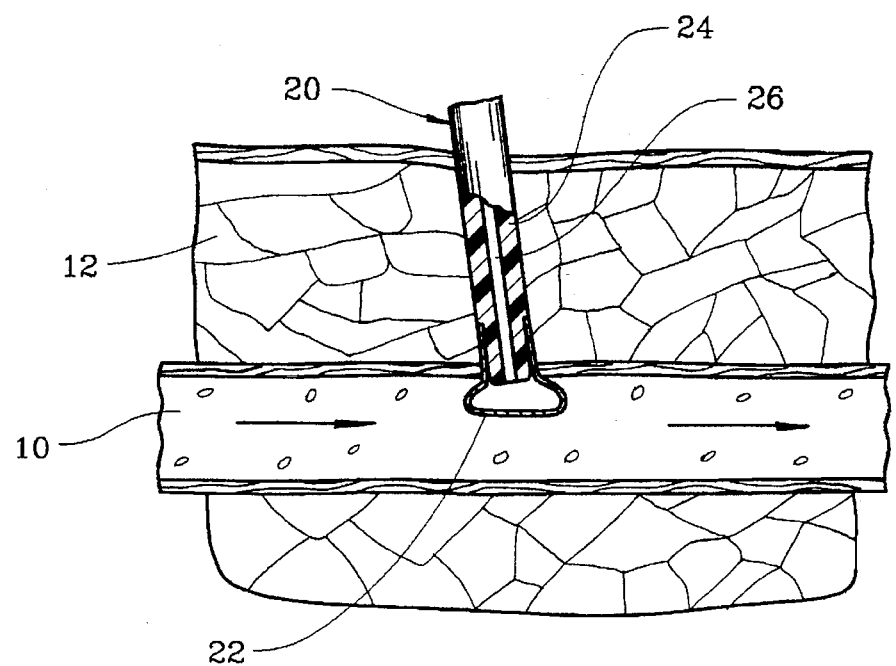
FIG. 3 is a side elevational view, partially in cross section, showing the balloon member of the sealing member of FIG. 1 inflated and positioned in the blood vessel of the patient.
Figure 2:
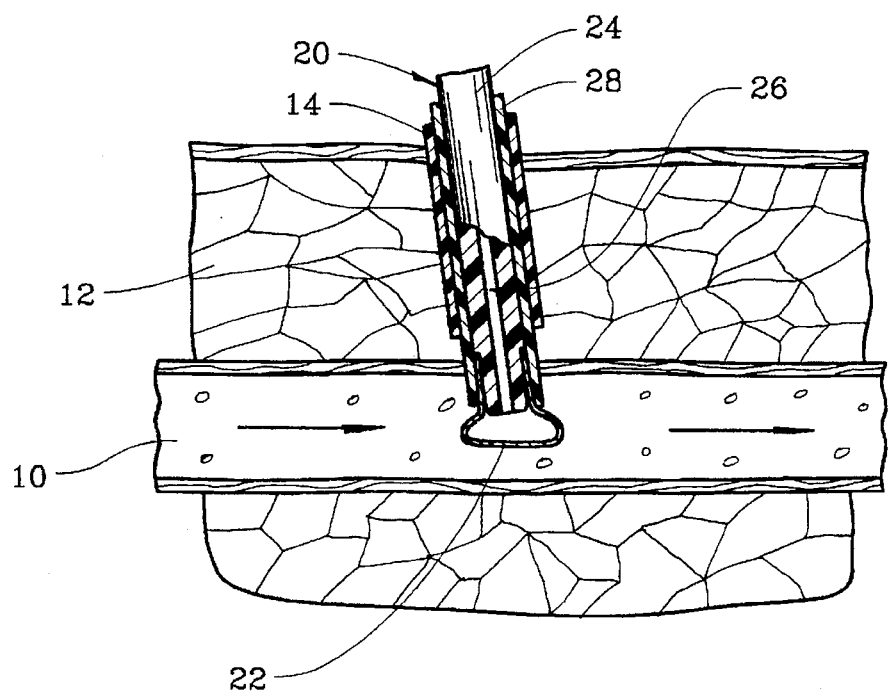
FIG. 2 is a side elevational view, partially in cross-section, showing the insertion of the sealing member and insertion sheath of the present invention into the incision in the patient.

As shown in FIGS. 1–3, the simplest and a preferred form of the present invention consists of a relatively small diameter sealing member 20 which includes a balloon member 22 or other manually expandable member securely attached to the distal end of an elongate shaft member 24. The shaft member 24 of the present embodiment preferably has a diameter approximately equal to or slightly less than the inner diameter of the catheter sheath 14 or the diameter of the incision formed in the body of the patient. Although the diameter of the shaft member 24 is preferably approximately equal to the diameter of the incision, it may also be slightly larger or smaller than the diameter of the incision without significantly reducing the effectiveness of the present invention due to the elasticity of the tissue surrounding the incision.

In this embodiment, the shaft member 24 includes a single lumen 26 extending therethrough in flow communication with the balloon member 22. The shaft member 24 is preferably constructed of a relatively stiff bioabsorbable material such as a lactide or glycolide polymer or copolymer as contained in the commercially available product MEDISORB manufactured by DuPont Co. Inc. or a similarly suitable bioabsorbable material. The stiffness of the shaft member 24 is chosen so that the sealing member 20 is immediately insertable into the incision and will not be readily crushed by the constriction of the tissue surrounding the incision but will still have sufficient porosity to enable the shaft member 24 to be absorbed into the body of the patient within weeks after insertion. The shaft member 24 is preferably molded or extruded to include the single lumen 26 which extends between the distal and proximal ends thereof.

In this embodiment, the balloon member 22 is preferably blow molded, extruded or otherwise formed and then fixedly attached to the shaft member 24 by bonding or other methods. The balloon member 22 is preferably constructed of a bioabsorbable or bioerodable polymeric elastomeric or non-elastomeric material such as a lactide or glycolide polymer or copolymer. Two such potential materials are a modified combination of dl-lactide and of polycaprolactone. The preferred material has the characteristics of having sufficient flexibility to be expanded after insertion into the blood vessel of the patient for a relatively short period of time while still having sufficient bioabsorbability to be dissolved by the blood flow in the blood vessel within a few days or weeks. Additionally, the interior surface of the balloon member 22 may be coated with a lubrication or other material to prevent the balloon member 22 from constricting or adhering to itself prior to use.

It is important to recognize that the intended use of the present balloon member 22 requires that the balloon member 22 have the ability to retain the fluid therein for a relatively short period of time until hemostasis in the incision has been achieved and therefore, the balloon member 22 of the present invention need not be as fluid tight as the balloon member or catheter devices used for angiographic or other procedures. Therefore, the preferred form of the balloon member 22 is constructed of a film-like material which has the ability to retain the saline solution in the balloon member 22 until the flow of blood from the blood vessel into the incision has been discontinued and the bleeding in the incision has stopped. As soon as this has occurred, the balloon member 22 is preferably harmlessly dissolved by the flow of blood in the blood vessel. Additionally, if any loose particles or fragments of the balloon member 22 are formed during the dissolution of the balloon member 22, these fragments are preferably harmlessly dissolved in the blood stream of the patient without forming potentially injurious occlusions downstream of the incision.

As shown in FIGS. 1–3, the insertion of the present embodiment is relatively simple and may include a number of safeguards which are described more fully below. Initially, the sealing member 29 is preferably positioned in an insertion sheath 28 which consists of an elongate and semi-rigid tubular member constructed of a suitable material such as a polyolefin, vinyl or fluorinated polymer. Once the angiographic or other procedure is completed, temporary manual pressure is applied to compress the artery upstream of the incision and the insertion sheath 28 is then inserted into the catheter sheath 14 until the distal end of the insertion sheath 28 extends slightly beyond the distal end of the catheter sheath 14 in the blood vessel of the patient. The sealing member 20 is then moved distally with respect to the insertion sheath 28 until the balloon member 22 has cleared the distal end of the insertion sheath 28 in the blood vessel of the patient.

Figure 6:
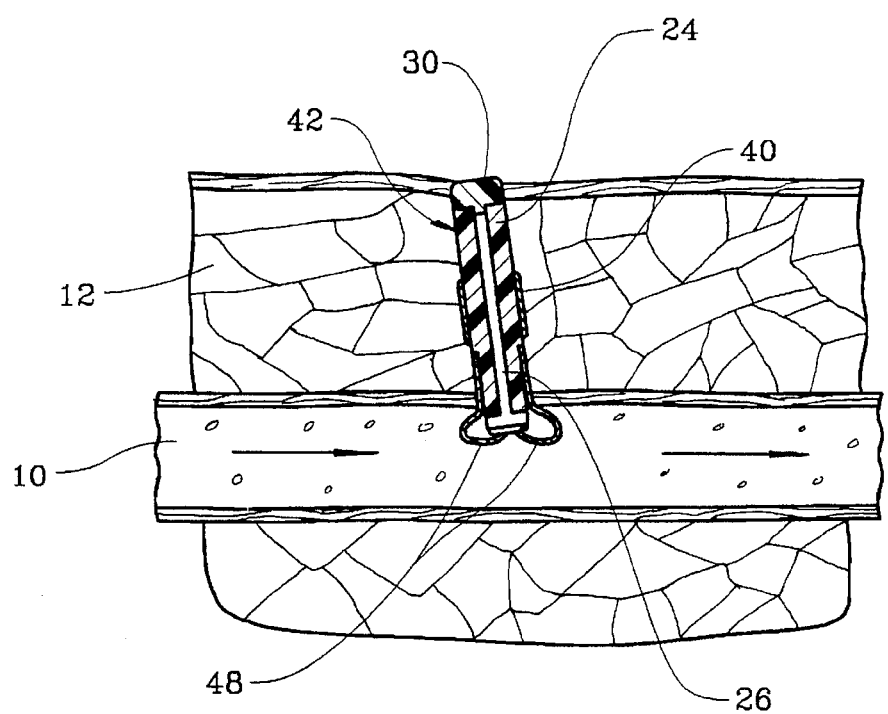
FIG. 6 is a partial side view showing the proximal portion of the sealing member of the embodiment shown in FIG. 4 with a plug member inserted therein.

A syringe assembly or other fluid containing member (not shown) is then attached to the proximal end of the shaft member 24 and the balloon member 22 is at least partially expanded by injecting a saline solution or other fluid preferably containing a radiopaque material therein into the sealing member 20. The catheter sheath 14 and the introducer sheath 28 are then at least partially withdrawn into the incision to allow the tissue surrounding the distal portion of the incision and the wall of the blood vessel to constrict around the shaft member 24 as shown in FIG. 2. The balloon member 22 is then fully expanded and the sealing member 20 is withdrawn in the incision until contact between the inner wall of the blood vessel adjacent to the incision and proximal surface of the balloon member 22 is detected by the user. Once this contact is detected, the balloon member 22 is withdrawn slightly to ensure that the balloon member 22 effectively seals the incision from the flow of blood through the incision. The catheter sheath and insertion sheath 28 may then be completely removed from the incision. Next, the shaft member 24 may be sutured to the skin near or slightly below the outer surface of the skin of the patient to retain the sealing member 20 in the desired position within the incision. The shaft member 24 may then be cut down or severed at or below the outer surface of the skin of the patient to remove the excess shaft member 24 extending above the skin surface of the patient. As shown in FIG. 6 and as described below, a bioabsorbable plug member 30 may then be inserted into the proximal end of the lumen 26 to prevent the premature loss of the fluid in the sealing member 20 through the lumen 26. Alternately, it may be possible to tie a suture around the shaft member 24 to compress the shaft member 24 thereby preventing the flow of fluid therethrough.

The present embodiment may also be inserted into the incision without the use of the insertion sheath 28. In this method of insertion, the distal end of the sealing member 20 is inserted into the blood vessel directly through the catheter sheath 14. Once the distal end of the sealing member 20 is moved to extend beyond the distal end of the catheter sheath 14, the catheter sheath 14 may be partially or completely withdrawn from the incision. The balloon member 22 may then be expanded by injecting the saline solution into the sealing member 20. The balloon member 22 is then withdrawn in the incision until the proximal surface of the balloon member 22 contacts the inner wall of the blood vessel. The sealing member 20 may then be securely positioned in the incision by suturing the shaft member 24 to the tissue surrounding the incision as described above and, if the user desires, the fluid may be removed from the sealing member 20 to deflate the balloon member 22 once hemostasis has been achieved in the incision.

Once the sealing member 20 is positioned in the incision as shown in FIG. 3, the balloon member 22 is designed to preferably dissolve within a matter of days and harmlessly release the fluid, if any, from the balloon member 22 into the blood stream of the patient. The shaft member 24 is designed to be preferably absorbed into the body of the patient within a matter of weeks so that after a few months, the entire sealing member 20 will be completely absorbed in the majority of patients.

The present invention is designed to allow the user to safely verify the location of the balloon member 22 during each step of the insertion procedure. This is accomplished by allowing the user to inject a radiopaque material into the sealing member 20 and then visually confirm the exact location or configuration of the balloon member 22 using conventional visualization methods whenever the user desires to determine the location of the balloon member 22 during the insertion procedure. Additionally, the sealing member 20 is readily removable from the incision if the balloon member 22 is improperly placed in the incision. This may be accomplished by withdrawing the plunger of the syringe assembly or by removing the syringe assembly from the proximal end of the shaft member 24 to deflate the balloon member 22. Due to the stiffness of the shaft member 24, the user may then withdraw the sealing member 20 from the incision. Finally, if the balloon member 22 fails to inflate or bursts during inflation, the sealing member 20 is readily removable from the incision and, if any fragments of the film-like balloon member 22 detach from the sealing member 20, the fragments will quickly dissolve in the blood stream of the patient.

Figure 4:
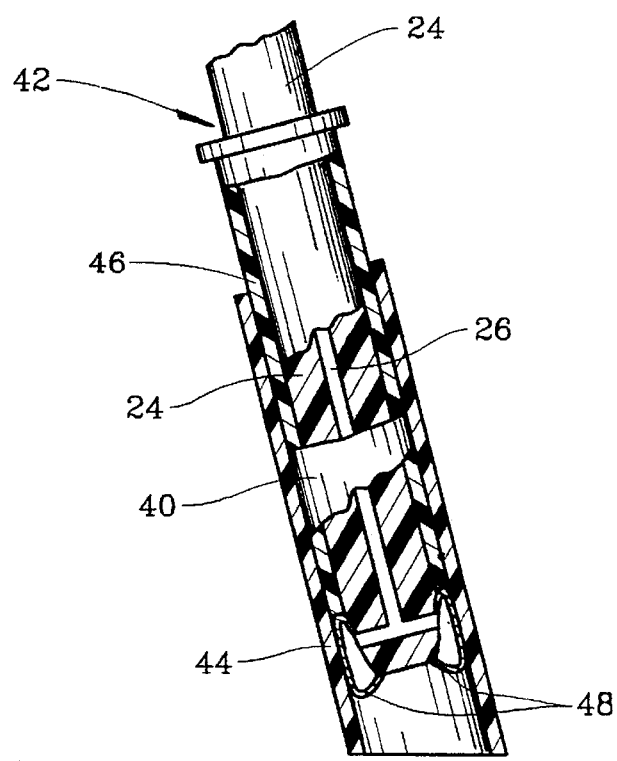
FIG. 4 is a side elevational view showing an alternate embodiment of the present invention, partially in cross section, showing the sealing member having a pair of balloon members thereon and a hemostatic collagen member in an insertion sheath prior to insertion of the present embodiment into the patient.
Figure 5:
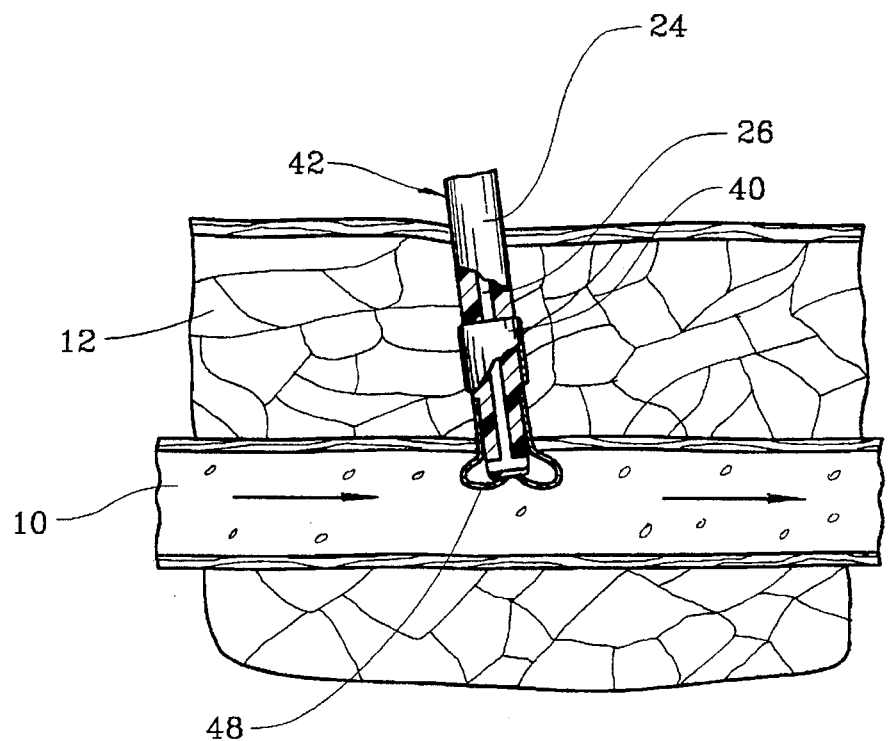
FIG. 5 is a side elevational view of the embodiment shown in FIG. 4, partially in cross section, showing the sealing member and hemostatic collagen member positioned in the patient with the balloon members inflated.

As shown in FIGS. 4–6, the present invention may also include a bioabsorbable hemostatic or collagen member 40 slidably positioned about the outer diameter of the modified sealing member 42. The collagen member 40 of this embodiment is preferably an expandable hemostatic collagen sponge or a similar bioabsorbable and expandable hemostatic material such as the collagen cuff sold by the Vitaphore Corporation under the name VITACUFF.

As shown in FIG. 4, the present embodiment preferably includes a modified insertion sheath 44.. The insertion sheath 44 of this embodiment is sized to receive the sealing member 42 and collagen member 40 therein and includes a plunger member 46 extending from the proximal end thereof. The plunger member 46 is sized to encircle a portion of the shaft member 24 of the catheter 42 and to contact the proximal side of the collagen member 40 while a portion of the plunger member 46 extends from the proximal end of the insertion sheath 44. The collagen member 40 may be compacted slightly against the inner walls of the insertion sheath 44 to create frictional contact therebetween while the interior surface of the collagen member 40 is preferably sized to allow the shaft member 24 to be slidable therethrough.

The sealing member 42 of this embodiment includes a pair of balloon members 48 on the distal end thereof and may include one or more lumens 26 extending through the shaft member 24 in flow communication therewith. The balloon members 48 of the present embodiment perform the same function as the balloon member 22 of the prior embodiment except that the distal end of the shaft member 24 is positioned closer to the inner wall of the blood vessel than in the prior embodiment when the balloon members 48 are inflated. The use of the dual balloon members 48 on the distal end of the sealing member 42 preferably provide for a flatter cross-sectional profile along the inner wall of the blood vessel than in the prior embodiment and the proximal surfaces of the balloon members 48 may be affixed to the shaft member 24 proximally of the distal end thereof as shown in FIG. 6 to create further resistance to the inadvertent removal of the sealing member 42 from the incision.

Insertion of this embodiment into the incision of the patient is generally similar to the method of insertion of the preferred embodiment described above. Initially, the insertion sheath 44 containing the sealing member 20 and collagen member 40 therein are inserted into the catheter sheath 14. Prior to the next step, the distal end of the catheter sheath 14 is preferably positioned to extend only slightly into the incision or blood vessel of the patient. The insertion sheath 44 is then moved with respect to the catheter sheath 14 such that the distal end of the insertion sheath 44 extends distally a short distance beyond the catheter sheath 14 in the blood vessel of the patient. The sealing member 42 is then moved distally with respect to the insertion sheath 44 such that the balloon members 48 extends beyond the distal end of the insertion sheath 42 in the blood vessel of the patient. A syringe assembly or other fluid containing member (not shown) is then used to manually expand the balloon members 48 by injecting a saline solution or other fluid into the lumen 26 of the sealing member 20. The catheter sheath 14 and insertion sheath 44 are then at least partially withdrawn from the incision and the sealing member 20 is moved proximally in the incision until the proximal sides of the balloon members 48 contact the inner wall of the blood vessel. The catheter sheath 14 and insertion sheath 44 are then completely withdrawn from the incision while the shaft member 24 of the sealing member 42 is allowed to slide in the insertion sheath 44 so that the contact between the balloon members 48 and the blood vessel is maintained. As shown in FIG. 5, this additional withdrawal of the catheter sheath 14 and insertion sheath 44 allows the tissue surrounding the incision adjacent to the blood vessel to contract around the shaft member 24. Alternately, due to the slightly larger radial diameter of the balloon members 48 of this embodiment, the catheter sheath 14 may be withdrawn from the incision once the balloon members 48 are initially inflated. Next, the insertion sheath 44 and the sealing member 20 may be withdrawn together in the incision until the balloon members 48 contact the inner wall of the blood vessel whereupon the withdrawal of the insertion sheath 44 is continued after contact between the balloon members 48 and the blood vessel wall is detected.

Once the balloon members 48 are positioned adjacent to the wall of the blood vessel, the user depresses the plunger member 46 to move the collagen member 40 distally in the incision to a location in the incision which is preferably adjacent to the outer wall of the blood vessel. The distal end of the collagen member 40 is constructed to expand and absorb any blood or fluid which may be trapped in the incision between the distal end of the insertion sheath 44 and the balloon members 48. This expansion of the distal end of the collagen member 40 causes the tissue surrounding the incision to expand thereby securely retaining the collagen member 40 in the incision. Additionally, the distal portion of the collagen member 40 also collapses about the shaft member 24 to frictionally retain the sealing member 42 in the desired position in the incision. Once the balloon members 48 and collagen member 40 are in position in the incision, the proximal portion of the shaft member 24 may be excised at or below the outer surface of the skin of the patient. If the user desires to retain the fluid in the sealing member 42, the user may insert a plug member 30 into the proximal end of the shaft member 24 as shown in FIG. 6. In this embodiment, the balloon members 48 operate to close the incision and prevent the flow of blood from the blood vessel from entering the incision. The hemostasis in this embodiment is caused by the expansion of the collagen member 40 against the tissue surrounding the incision.

Therefore, once the collagen member 40 causes hemostasis, the balloon members 48 may be deflated without adversely affecting the operation of the present embodiment. Additionally, the smaller cross-sectional profile of the balloon members 48 of this embodiment are designed to minimize the short term disruption of the flow of blood through the blood vessel.

Figure 7:
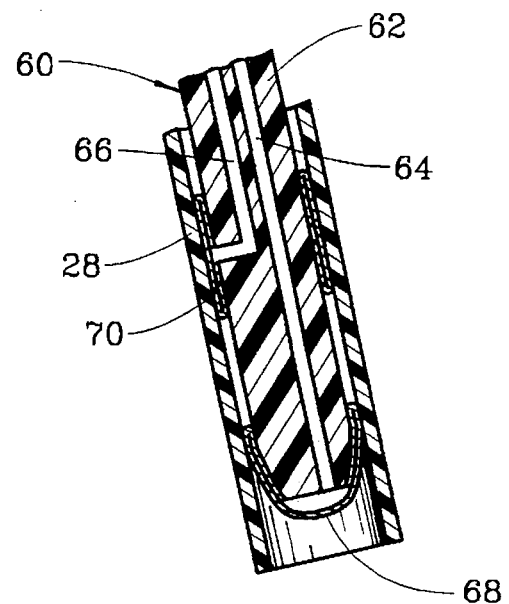
FIG. 7 is a side elevational view of an alternate embodiment of the present invention, partially in cross-section, showing a dual lumen catheter member having a pair of balloon members thereon inserted in an insertion sheath prior to insertion into the patient.
Figure 8:
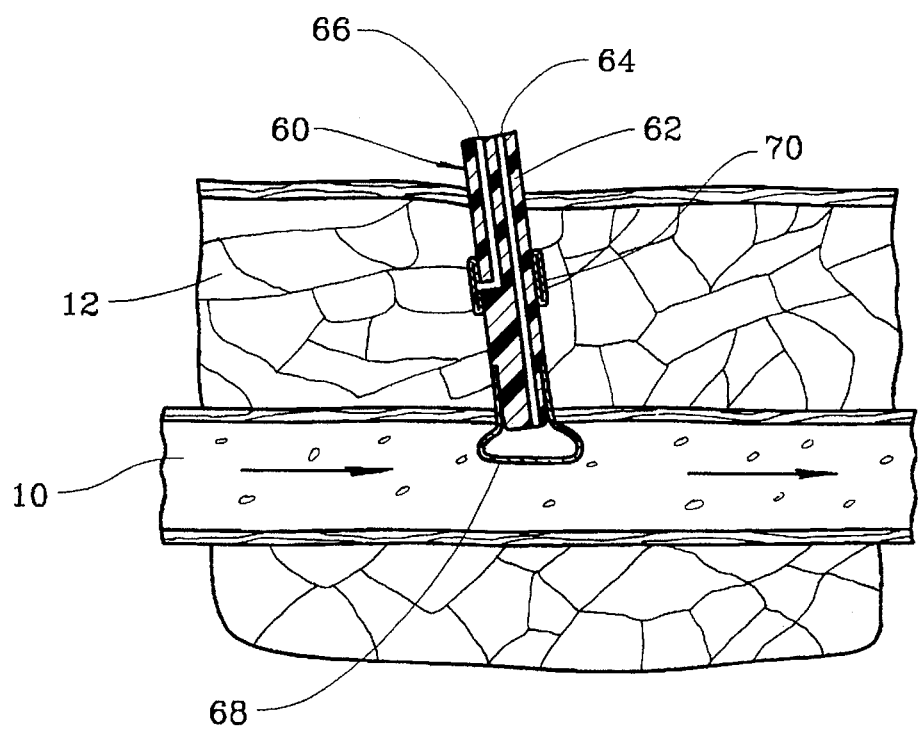
FIG. 8 is a side elevational view, partially in cross-section, showing the sealing member of FIG. 7 in the preferred position in the incision in the patient with the distal balloon member inflated.
Figure 9:
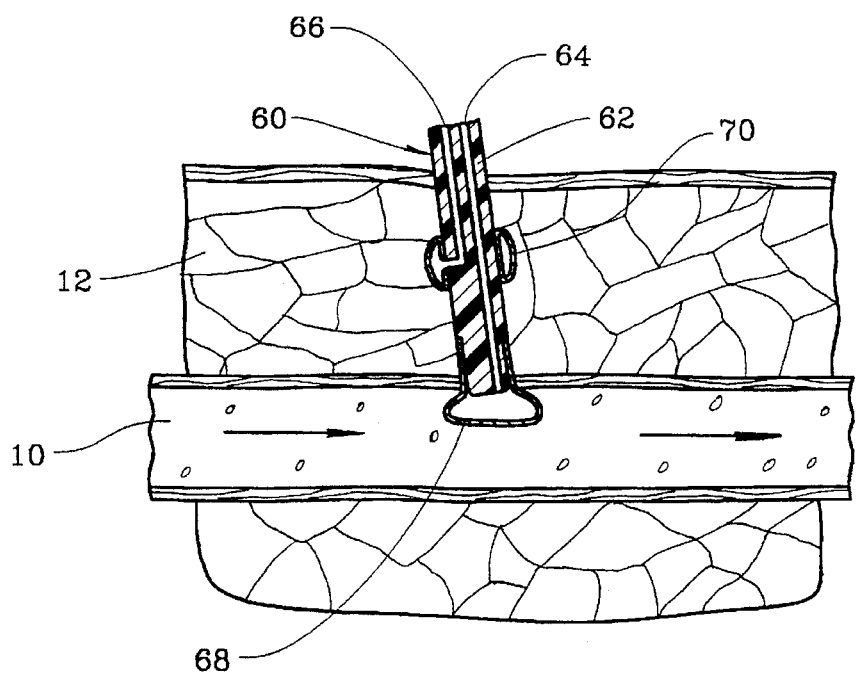
FIG. 9 is a side elevational view, partially in cross section showing the sealing member of FIG. 8 positioned in the incision with both of the balloon members inflated and inserted in the preferred position in the incision in the patient.

FIGS. 7–9 show a further embodiment of the present invention wherein the sealing member 60 is modified to include a shaft member 62 having first and second lumens, 64 and 66, extending therethrough. In this embodiment, the first lumen 64 is in flow communication with a flexible first balloon member 68 which is positioned generally along the distal end of the shaft member 62. The second lumen 66 is in flow communication with a second balloon member 70. The second balloon member 70 is longitudinally and proximally spaced apart from the first balloon member 68 along the shaft member 62.

FIG. 7 shows the sealing member 60 of the present embodiment positioned in an optional insertion sheath 28. When the insertion sheath 28 is used, the catheter sheath 14 is initially positioned in the incision and blood vessel such that the distal end of the catheter sheath 14 extends a relatively short distance into the blood vessel of the patient. The insertion sheath 28 is then inserted into the catheter sheath 14 such that the distal end of the insertion sheath 28 extends a short distance beyond the distal end of the catheter sheath 14 in the blood vessel. Next, the user grasps the shaft member 62 of the sealing member 60 and moves the sealing member 60 distally in the insertion sheath 28 until the first balloon member 68 extends beyond the distal end of the insertion sheath 28 in the blood vessel. A syringe assembly or other fluid containing member (not shown) is then inserted into the proximal end of the first lumen 64 of the sealing member 60. The first balloon member 68 is then inflated in the blood vessel of the patient by injecting a saline solution or other fluid into the first lumen 64 of the sealing member 60. Once the first balloon member 68 is inflated, the catheter sheath 14 and insertion sheath 28 are withdrawn from the blood vessel of the patient to an intermediate position approximately midway along the incision. The sealing member 60 is then withdrawn proximally in incision until the proximal side of the first balloon member 68 contacts the inner surface of the wall of the blood vessel. The contact between the balloon member 68 and the wall of the blood vessel seals the incision from the flow of blood therethrough. The catheter sheath 14 and insertion sheath 28 are then completely removed from the incision. A second syringe assembly or other fluid containing member (not shown) is then attached to the proximal end of the second lumen 66 and a fluid is injected therethrough to inflate the second balloon member 70. As the second balloon member 70 is inflated, the second balloon member 70 expands against the tissue surrounding the incision to securely retain the sealing member 60 in the desired position in the incision. If desired, the shaft member 62 may be excised below the outer surface of the skin of the patient and the lumens 64 and 66 may be sealed by a plug member 30 or suture to prevent the premature deflation of the balloon members 68 and 70 as described above. As shown in FIG. 9, the tissue surrounding the incision and the wall of the blood vessel contracts about the portion of the shaft member 62 between the first and second balloon members, 68 and 70, and the wall of the blood vessel. In the preferred form of this embodiment, the second balloon member 70 is oriented along the shaft member 62 to expand radially and slightly proximally or distally with respect to the shaft member 62 as the second balloon member 70 is inflated so that the wall of the blood vessel and more preferably, the blood vessel wall and a portion of the tissue surrounding the incision are compressed or otherwise securely retained between the first and second balloon members 68 and 70 to ensure that the sealing member 60 remains properly positioned in the incision. Once the sealing member 60 is inserted in the incision as described above, the first and second balloon members 68 and 70 are preferably dissolved within a few days and the shaft member 62 is preferably dissolved within a few weeks. As with the balloon members of the prior embodiments, the balloon members 68 and 70 of the present embodiment may be individually or both deflated once hemostasis has been achieved.

Figure 10:
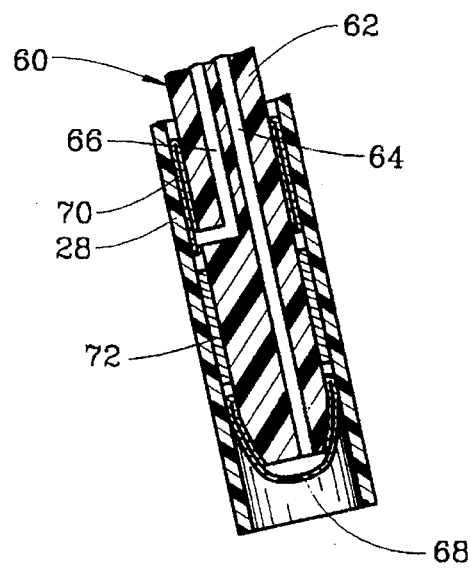
FIG. 10 is a side elevational view of an alternate embodiment of the present invention, partially in cross section showing a dual lumen sealing member with a pair of balloon members and a hemostatic collagen member thereon in an insertion sheath and prior to insertion in the patient.
Figure 11:
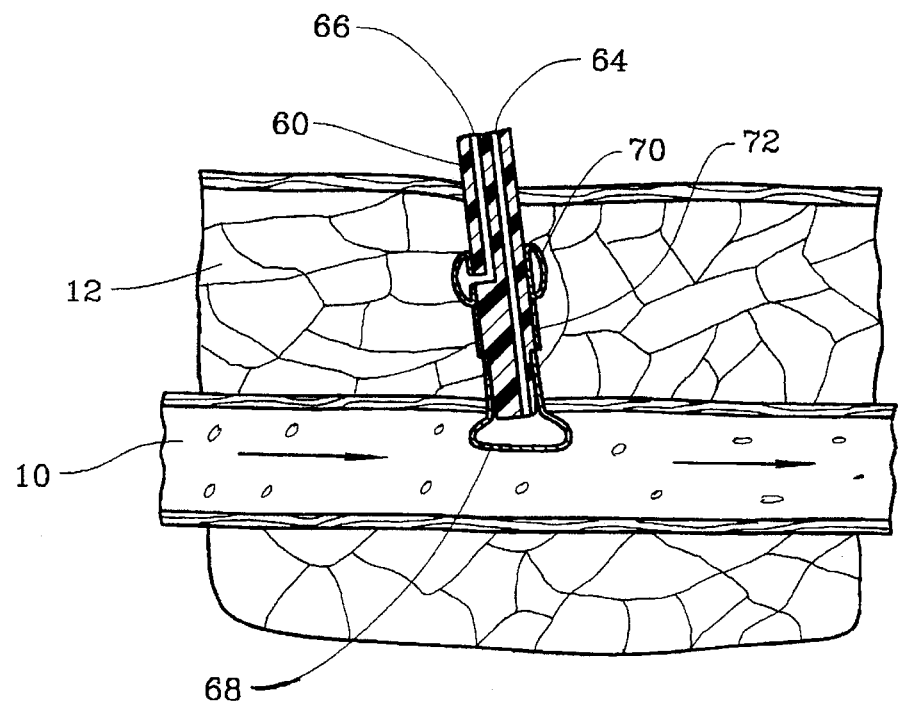
FIG. 11 is a side elevational view, partially in cross-section showing the sealing member of FIG. 10 after insertion of the present embodiment into the incision in the patient.

FIGS. 10–11 show an alternate embodiment of the present invention which is similar to the embodiment described above and shown in FIGS. 7–9. In this embodiment, a cylindrically shaped hemostatic member such as collagen member 72 is positioned around the portion of the shaft member 62 which is located between the first and second balloon members 68 and 70. FIG. 10 shows this alternate embodiment in the insertion sheath 28 prior to insertion of the sealing member 60 into the incision. As with the prior embodiment, the sealing member 60 includes a shaft member 62 having first and second lumens, 64 and 66, extending therethrough and first and second balloon members 68 and 70 thereon.

In this embodiment, the collagen member 72 is preferably frictionally or otherwise fixedly positioned distally of the second balloon member 70 on the shaft member 62. The length of the collagen member 72 is preferably chosen so that the distal end of the collagen member 72 is spaced apart from the distal end of the shaft member 62 and the first balloon member 68. The proximal end of the collagen member 72 is preferably positioned generally adjacent to the distal side of the second balloon member 70 as shown in FIG. 11. Alternately, it is believed that the collagen member 72 may extend completely between the distal side of the second balloon member 70 and the proximal side of the first balloon member 68 without adversely affecting the operation of the present embodiment.

The method of insertion of this embodiment into the incision is similar to the insertion method of the embodiment shown in FIGS. 7–9 and differs only in that the collagen member 72 is positioned in the incision to extend generally from a position near the outer wall of the blood vessel to the distal side of the second balloon member 70 as the sealing member 60 is inserted in the incision. In the alternate form of this embodiment, the elongated collagen member (not shown) is designed to extend between the first and second balloon members 68 and 70 and through the wall of the blood vessel.

In the embodiment shown in FIGS. 10 and 11, the first balloon member 68 functions to seal the incision from the flow of blood through the blood vessel. The collagen member 72 expands and promotes hemostasis in the incision and the second balloon member 70 assists in ensuring that the collagen member 72 and first balloon member 68 are properly positioned in the incision. The shaft member 62 in this embodiment and the embodiment shown in FIGS. 7–9 may be severed further below the outer surface of the skin near the proximal side of the second balloon member 70 than in the prior embodiments because the balloon members 68 and 70 of these embodiments retain the remaining portion of the sealing member 60 in position within the incision, with the proximal portion of the shaft member 62 merely providing access to the balloon members 68 and 70 during the insertion of these embodiments into the incision in the patient.

Figure 12:
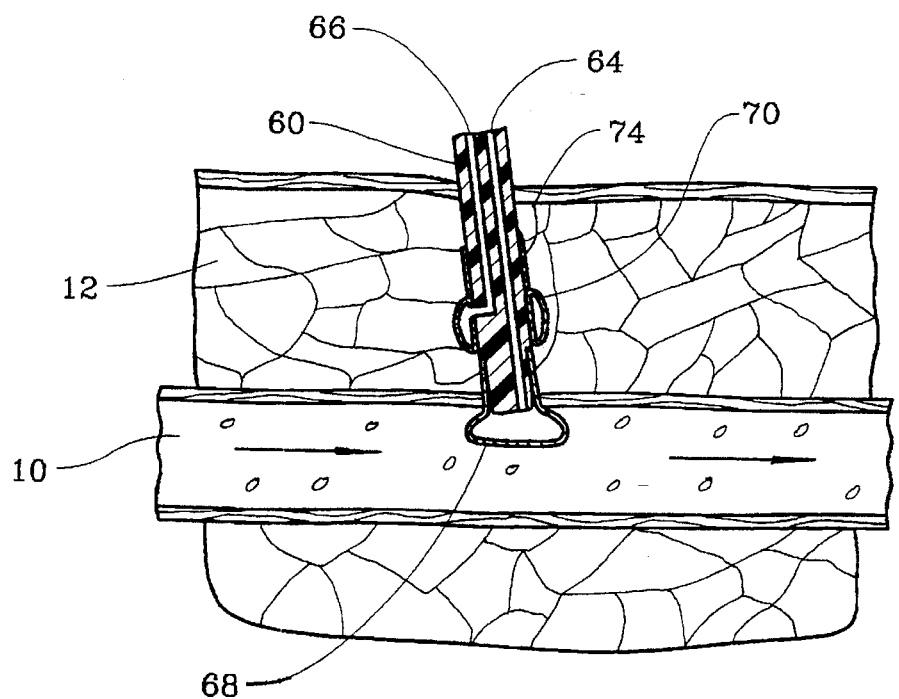
FIG. 12 is a side elevational view of an alternate embodiment of the present invention, partially in cross-section showing the sealing member and hemostatic collagen member in the incision in the patient with a hemostatic collagen member positioned proximally of the balloon members.

FIG. 12 illustrates yet another embodiment of the present invention. This embodiment is similar to the embodiments shown in FIGS. 7–9 and 10–11. In this embodiment, the hemostatic collagen member 74 is slidable along the shaft member 62 and into contact with the proximal side of the second balloon member 70. In this embodiment, the first and second balloon members 68 and 70 function to retain a portion of the tissue surrounding the incision and the wall of the blood vessel therebetween to seal the incision from the flow of blood from the blood vessel therethrough and to securely retain the sealing member 60 in the desired position in the incision. The collagen member 74 of this embodiment promotes hemostasis in the incision and absorbs fluids from the tissue surrounding the incision to prevent the weeping of fluids from the incision onto the outer surface of the skin of the patient.

Figure 13:
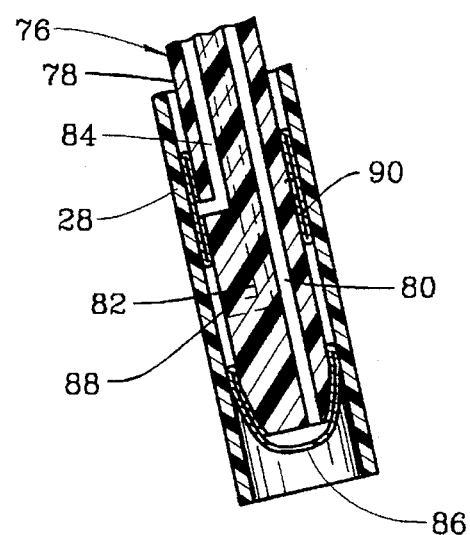
FIG. 13 is a side elevational view of an alternate embodiment of the present invention, partially in cross-section showing a triple lumen sealing member in an insertion sheath prior to insertion into the incision in the patient.
Figure 14:
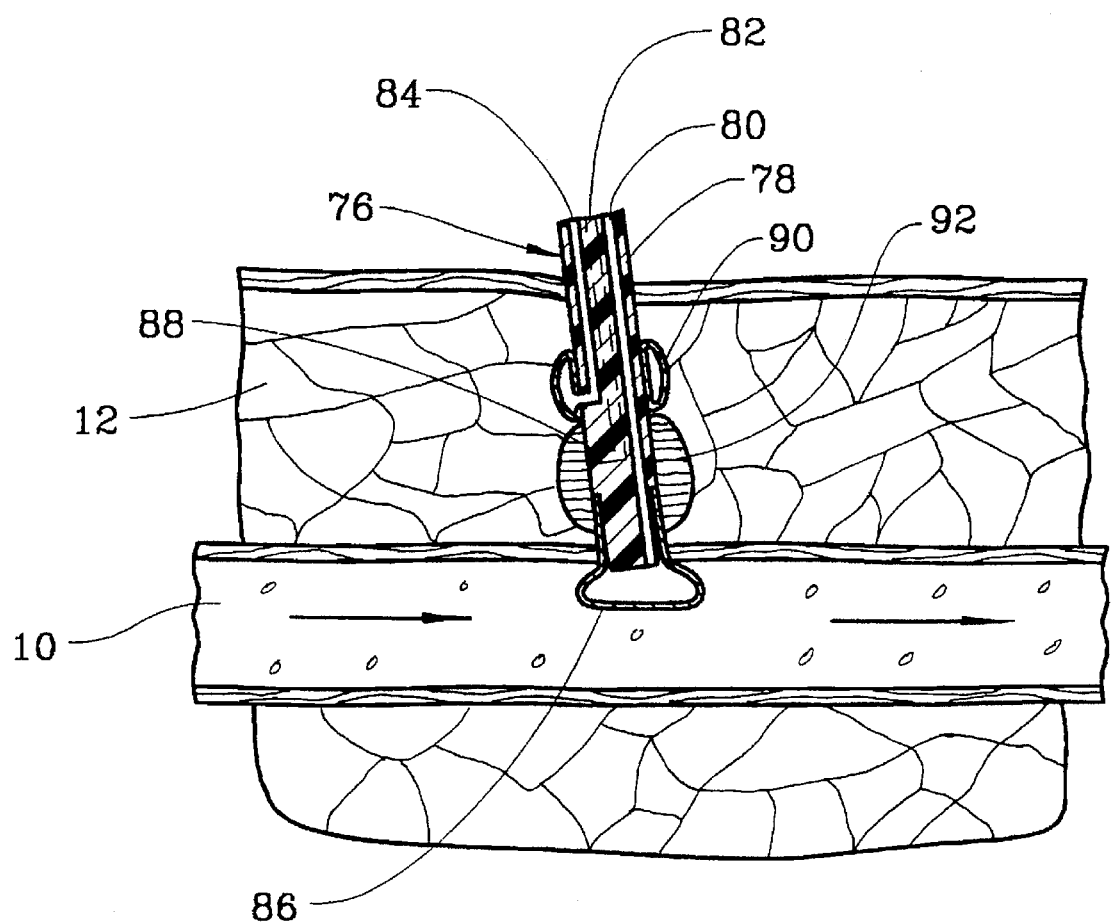
FIG. 14 is a side elevational view, partially in cross-section, of the embodiment of FIG. 13 showing the sealing member inserted in the incision in the patient with an injectable collagen member positioned between the balloon members.

FIGS. 13 and 14 show a further embodiment of the present invention wherein the sealing member 76 includes a shaft member 78 having first, second and third lumens 80, 82 and 84 therein, respectively. The first lumen 80 is in flow communication with the first balloon member 86. The first balloon member 86 is preferably positioned along the distal end of the shaft member 78. The second lumen 82 is in flow communication with an opening 88 along the portion of the shaft member 78 which is preferably positioned between the first balloon member 86 and the second balloon member 90. The third lumen 84 is in flow communication with the second balloon member 90. The second balloon member 90 is preferably proximally spaced apart from the distal end of the shaft member 78 and opening 88 along the shaft member 78.

In this embodiment, the sealing member 76 is preferably inserted into the incision in a manner similar to one or more of the insertion methods described above. As described above, the first balloon member 86 is initially inflated and positioned such that the proximal surface of the first balloon member 86 is adjacent to the inner surface of the wall of the blood vessel. The second balloon member 90 is then inflated to engage and contact the tissue surrounding the incision at a location in the incision proximally of the blood vessel. Next, a commercially available injectable collagen 92 may be injected into the second lumen 82 and through the opening 88 in the sealing member 76. Collagen Corp. of Palo Alto, Calif., U.S.A. markets one such injectable collagen under the name of ZYDERM. As the injectable collagen 92 is injected through the sealing member 76, the injectable collagen 92 initially flows around the shaft member 78 to fill in any voids or irregularities in the tissue surrounding the incision. As more injectable collagen 92 is forced through the opening 88, the injectable collagen 92 causes the tissue surrounding the incision to expand thereby further ensuring that the flow of blood from the blood vessel is prevented from entering the incision. In this embodiment, the inflated first and second balloon members 86 and 90 inhibit the flow of injectable collagen 92 distally or proximally beyond the first and second balloon members 86 and 90. The injectable collagen 92 further promotes hemostasis within the incision and allows the surrounding tissue to infiltrate the collagen matrix as the injectable collagen 92 is absorbed into the body of the patient.

In the foregoing embodiment, various forms of the sealing member and collagen member are disclosed, it is anticipated that the various features described above with respect to the embodiments of the present invention may be interchanged or modified without departing from the basic invention which is defined by the following claims. Although the above described shaft members of the sealing members are preferably constructed of a relatively stiff bioabsorbable material such as lactide or glycolide polymers or copolymers, the sealing members may be constructed of a number of bioabsorbable materials as long as the elements of the sealing members have the qualities necessary to perform the desired functions as described above. The above described balloon members may also be constructed of a number of different materials as long as the bioabsorbability and flexibility of the balloon member is retained to enable the balloon member to perform the sealing and hemostatic functions as described above. Similarly, the collagen members or injectable collagen as described above may be constructed of a number of bioabsorbable materials as long as the collagen members or injectable collagen have the qualities necessary to perform the desired hemostatic functions as described above.

What is claimed is:

1. A device for sealing an incision which extends between the skin and a blood vessel in the body of a patient, the device comprising:

a bioabsorbable member for sealing the incision wherein said bioabsorbable member includes a first member having an elongate shaft member having a lumen therein and an expandable member operatively associated therewith, said shaft member and expandable member being sized to extend through the incision and at least one of said first member and said expandable member being constructed in such a manner so as to be absorbable within the body of the patient after a period of time sufficient for permitting the effective sealing of the incision.

2. The device of claim 1 wherein said expandable member includes a first radial diameter for insertion of said first member through the incision and a second radial diameter for operatively retaining said shaft member in a predetermined position in the incision in use.

3. The device of claim 1 wherein said shaft member is an elongate member having a lumen extending therethrough and wherein said lumen is in communication with said expandable member.

4. An assembly for sealing or closing an incision or puncture in the body of a living patient wherein the incision or puncture extends into a blood vessel of the patient, the assembly comprising:

a bioabsorbable elongate shaft member having a proximal end and a distal end and having a bioabsorbable expandable member disposed at said distal end, said expandable member constructed to be positioned alternatively in a relaxed condition and an expanded condition;

said shaft member and said expandable member dimensioned to be inserted within the puncture so that said expandable member is positioned within a blood vessel of the patient;

control member associated with said shaft member and in communication with said expandable member for selectively positioning said expandable member between said expanded condition and said relaxed condition; and a slidable member operatively associated with said shaft member for insertion into the incision or puncture, said expandable member configured to cooperate with said slidable member when said expandable member is in said expanded condition to prevent said slidable member from extending into the blood vessel of the patient.

5. The assembly as defined in claim 4 further including an introducer having a lumen extending longitudinally therethrough, said introducer dimensioned to receive said shaft member and said expandable member within said lumen.

6. An assembly for sealing or closing an incision or puncture in the body of a living patient wherein the incision or puncture extends into a blood vessel or an organ of the patient, the assembly comprising:

a bioabsorbable elongate shaft member having a proximal end and a distal end and having a bioabsorbable expandable member disposed at said distal end, said expandable member constructed to be positioned alternatively in a relaxed condition and an expanded condition;

said shaft member and said expandable member dimensioned to be inserted within the puncture so that said expandable member is positioned within a target organ or blood vessel of the patient;

control member associated with said shaft member and in communication with said expandable member for selectively positioning said expandable member between said expanded condition and said relaxed condition;.

a slidable member operatively associated with said shaft member for insertion into the incision or puncture, said expandable member configured to cooperate with said slidable member when said expandable member is in said expanded condition to prevent said slidable member from extending into the blood vessel or the organ of the patient; and wherein said slidable member is a cylindrical member constructed of a biodegradable material.

7. An apparatus for sealing or closing an incision or puncture in the body of a living patient wherein the incision or puncture extends into a blood vessel or an organ of the patient, the apparatus comprising:

a bioabsorbable tubular member having a proximal end and a distal end and having an expandable member disposed at said distal end of said tubular member, said expandable member constructed to be absorbed in the body of the patient and positioned alternatively in a relaxed condition and an expanded condition;

said expandable member dimensioned to be positioned within a target organ or blood vessel of the patient and constructed to permit blood and other body fluids to pass through the blood vessel or target organ while said expandable member is positioned therein; and a bioabsorbable vessel plug operatively associated with said tubular member and said expandable member, said vessel plug dimensioned to obstruct the flow of fluids through the puncture or incision and said expandable member, when in said expanded condition within the blood vessel or the target organ, preventing said vessel plug from extending into the vessel or the target organ.

8. The apparatus of claim 7 wherein said vessel plug is a cylindrical rod shaped member constructed of a biodegradable material.

9. The apparatus of claim 7 further including an introducer having a lumen extending longitudinally therethrough, said introducer dimensioned to receive said tubular member and said expandable member within said lumen.

10. A method for sealing or closing an incision or puncture in the body of the living patient wherein the incision or puncture extends into a blood vessel of the patient, the method comprising:

inserting an elongated member into the incision, the elongated member being formed of a bioabsorbable material and having a distal end and a proximal end and having an expandable member disposed at the distal end, the expandable member constructed to be positioned alternatively in a relaxed condition and an expanded condition;

expanding the expandable member within the blood vessel and permitting blood to pass through the blood vessel while the expandable member is positioned therein;

positioning a surface of the expandable member adjacent the incision or puncture in the blood vessel; and inserting a vessel plug into the incision or puncture proximally of the expandable member and the expandable member operating in the expanded condition to prevent the vessel plug from extending into the blood vessel of the patient.

11. The method of claim 10 wherein the insertion of an elongated member into the incision is accomplished by inserting the elongate member through a sheath introducer extending from the skin of the patient and into the blood vessel.

12. A method for sealing or closing an incision or puncture in the body of the living patient wherein the incision or puncture extends into a blood vessel or target organ of the patient, the method comprising:

inserting an elongated member into the incision, the elongated member being formed of a bioabsorbable material and having a distal end and a proximal end and having an expandable member disposed at the distal end, the expandable member constructed to be positioned alternatively in a relaxed condition and an expanded condition;

expanding the expandable member within the blood vessel or target organ and permitting blood or other body fluids to pass through the blood vessel or target organ while the expandable member is positioned therein;

positioning a surface of the expandable member adjacent the incision or puncture in the blood vessel or the target organ;

inserting a vessel plug into the incision or puncture proximally of the expandable member and the expandable member operating in the expanded condition to prevent the vessel plug from extending into the blood vessel or target organ of the patient; and wherein the insertion of the vessel plug includes providing the plug as a cylindrical member made of a biodegradable material and inserting the plug in the incision or puncture to contact the surface of the expandable member adjacent to the incision.

* * * * *